United States Patent
Hu et al.

(10) Patent No.: US 12,426,840 B2
(45) Date of Patent: Sep. 30, 2025

(54) SYSTEMS AND METHODS FOR IMAGE SCANNING

(71) Applicant: SHANGHAI UNITED IMAGING HEALTHCARE CO., LTD., Shanghai (CN)

(72) Inventors: Lingzhi Hu, Houston, TX (US); Yiran Li, Houston, TX (US); Xishan Sun, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 49 days.

(21) Appl. No.: 18/465,955

(22) Filed: Sep. 12, 2023

(65) Prior Publication Data

US 2024/0081750 A1 Mar. 14, 2024

(30) Foreign Application Priority Data

Sep. 13, 2022 (CN) .......................... 202211107517.1

(51) Int. Cl.
*A61B 5/00* (2006.01)
*A61B 5/055* (2006.01)
*G06T 7/246* (2017.01)
*G06T 7/62* (2017.01)

(52) U.S. Cl.
CPC .......... *A61B 5/7285* (2013.01); *A61B 5/0037* (2013.01); *A61B 5/055* (2013.01); *G06T 7/246* (2017.01); *G06T 7/62* (2017.01); *A61B 2560/0223* (2013.01); *G06T 2207/10016* (2013.01); *G06T 2207/10088* (2013.01); *G06T 2207/20081* (2013.01); *G06T 2207/30004* (2013.01)

(58) Field of Classification Search
CPC ..... A61B 5/7285; A61B 5/0037; A61B 5/055; G06T 2207/10016; G06T 2207/10088; G06T 2207/20081; G06T 2207/30004
See application file for complete search history.

(56) References Cited

U.S. PATENT DOCUMENTS

| | | | |
|---|---|---|---|
| 8,069,125 B2 | 11/2011 | Jung et al. |
| 8,150,796 B2 | 4/2012 | Jung et al. |
| 8,195,593 B2 | 6/2012 | Jung et al. |
| 8,353,837 B2 | 1/2013 | John et al. |

(Continued)

FOREIGN PATENT DOCUMENTS

| | | |
|---|---|---|
| EP | 3865061 A1 | 8/2021 |
| EP | 3978071 A1 | 4/2022 |

(Continued)

*Primary Examiner* — Joel F Brutus
(74) *Attorney, Agent, or Firm* — METIS IP LLC

(57) ABSTRACT

Embodiments of the present disclosure provide a method and a system for image scanning. The method may include: obtaining image data of a subject, the image data being acquired by a scanning device scanning the subject during a time period; determining, based on the image data, a motion state of the subject in a motion cycle; obtaining a physiological signal of the subject in the motion cycle; determining, based on the motion state of the subject and the physiological signal of the subject, scan gating information of the subject; and determining, based on the scan gating information, target image data of the subject.

20 Claims, 6 Drawing Sheets

(56) References Cited

U.S. PATENT DOCUMENTS

| | | |
|---|---|---|
| 8,356,004 B2 | 1/2013 | Jung et al. |
| 8,868,174 B2 | 10/2014 | Sato et al. |
| 9,005,126 B2 | 4/2015 | Beach et al. |
| 9,211,077 B2 | 12/2015 | Jung et al. |
| 9,418,368 B2 | 8/2016 | Jung et al. |
| 9,495,684 B2 | 11/2016 | Jung et al. |
| 9,655,573 B2 | 5/2017 | Majewski et al. |
| 9,775,554 B2 | 10/2017 | Jung et al. |
| 2005/0214761 A1 | 9/2005 | Lerchl et al. |
| 2006/0079773 A1 | 4/2006 | Mourad et al. |
| 2008/0262327 A1 | 10/2008 | Kato |
| 2008/0287821 A1 | 11/2008 | Jung et al. |
| 2009/0018407 A1 | 1/2009 | Jung et al. |
| 2009/0156955 A1 | 6/2009 | Jung et al. |
| 2009/0157481 A1 | 6/2009 | Jung et al. |
| 2009/0157625 A1 | 6/2009 | Jung et al. |
| 2009/0157660 A1 | 6/2009 | Jung et al. |
| 2009/0157751 A1 | 6/2009 | Jung et al. |
| 2009/0157813 A1 | 6/2009 | Jung et al. |
| 2009/0164131 A1 | 6/2009 | Jung et al. |
| 2009/0164302 A1 | 6/2009 | Jung et al. |
| 2009/0164458 A1 | 6/2009 | Jung et al. |
| 2009/0164503 A1 | 6/2009 | Jung et al. |
| 2009/0171164 A1 | 7/2009 | Jung et al. |
| 2009/0318773 A1 | 12/2009 | Jung et al. |
| 2011/0301448 A1 | 12/2011 | Decharms |
| 2012/0083647 A1 | 4/2012 | Scheinin et al. |
| 2014/0135642 A1 | 5/2014 | Ekpar |
| 2014/0210469 A1* | 7/2014 | Cheng ............. G01R 33/56509 324/309 |
| 2015/0005841 A1 | 1/2015 | Pal et al. |
| 2015/0151142 A1 | 6/2015 | Tyler et al. |
| 2015/0216762 A1 | 8/2015 | Oohashi et al. |
| 2017/0258390 A1 | 9/2017 | Howard |
| 2017/0311832 A1 | 11/2017 | Barthelemy et al. |
| 2019/0082990 A1 | 3/2019 | Poltorak |
| 2019/0159716 A1 | 5/2019 | Alailima et al. |
| 2019/0201691 A1 | 7/2019 | Poltorak |
| 2019/0247662 A1 | 8/2019 | Poltorak |
| 2019/0377051 A1* | 12/2019 | Bacher ................. G16H 40/63 |
| 2020/0037942 A1 | 2/2020 | Howard |
| 2020/0060566 A1 | 2/2020 | Howard |
| 2020/0086078 A1 | 3/2020 | Poltorak |
| 2020/0139118 A1 | 5/2020 | John et al. |
| 2020/0352524 A1* | 11/2020 | Hu ....................... G01S 13/867 |
| 2020/0353059 A1 | 11/2020 | Lester et al. |
| 2020/0360715 A1 | 11/2020 | Lim |
| 2020/0368491 A1 | 11/2020 | Poltorak |
| 2020/0376287 A1 | 12/2020 | Rolls et al. |
| 2020/0402643 A1 | 12/2020 | Trees et al. |
| 2021/0005306 A1 | 1/2021 | Anticevic et al. |
| 2021/0031034 A1 | 2/2021 | Santarnecchi et al. |
| 2021/0085180 A1 | 3/2021 | Jung et al. |
| 2021/0123999 A1* | 4/2021 | An ................... G01R 33/56308 |
| 2021/0393991 A1 | 12/2021 | Miskovic et al. |
| 2021/0401289 A1 | 12/2021 | Yamashita et al. |
| 2022/0054853 A1 | 2/2022 | Bystritsky et al. |
| 2022/0062661 A1 | 3/2022 | Tyler |
| 2022/0240851 A1 | 8/2022 | Bower et al. |
| 2022/0280807 A1 | 9/2022 | Van De Ven et al. |
| 2023/0240584 A1 | 8/2023 | Shahaf |

FOREIGN PATENT DOCUMENTS

| | | |
|---|---|---|
| JP | 2009112266 A | 5/2009 |
| JP | 2014087355 A | 5/2014 |
| WO | 2008143908 A2 | 11/2008 |
| WO | 2015006827 A1 | 1/2015 |
| WO | 2015166279 A1 | 11/2015 |
| WO | 2016073482 A1 | 5/2016 |
| WO | 2018081134 A1 | 5/2018 |
| WO | 2018132483 A1 | 7/2018 |
| WO | 2019028376 A1 | 2/2019 |
| WO | 2019173189 A1 | 9/2019 |
| WO | 2020081609 A1 | 4/2020 |
| WO | 2020236956 A1 | 11/2020 |
| WO | 2021173564 A1 | 9/2021 |
| WO | 2021207356 A1 | 10/2021 |
| WO | 2022053587 A1 | 3/2022 |
| WO | 2022069755 A1 | 4/2022 |

* cited by examiner

SYSTEMS AND METHODS FOR IMAGE SCANNING

CROSS-REFERENCE TO RELATED APPLICATIONS

This application claims priority to Chinese Patent Application No. 202211107517.1, filed on Sep. 13, 2022, the entire contents of which are incorporated herein by reference.

TECHNICAL FIELD

The present disclosure relates to the field of image processing, in particular, to a system and a method for image scanning.

BACKGROUND

When scanning a subject (e.g., the heart, a liver, the abdomen, etc.), the subjects (e.g., the heart, the liver, the lung, etc.) during the scanning may move. When performing a magnetic resonance (MR) scanning on these movable subjects, a scanning trigger point is generally determined based on a default motion cycle. If there is a significant difference between the default motion cycle and an actual motion cycle of the subject, the actual image obtained by scanning may not meet the requirements, thus requiring to perform a re-scanning, causing resource waste and reducing work efficiency.

Therefore, it is desirable to provide a system and a method for image scanning, to determine a more accurate scanning trigger mechanisms for different movable subjects.

SUMMARY

An aspect of the present disclosure provides a system. The system may include at least one storage medium including a set of instructions; and at least one processor in communication with the at least one storage medium. When executing the set of instructions, the at least one processor may be directed to cause the system to perform operations. The operations may include obtaining image data of a subject. The image data may be acquired by a scanning device scanning the subject during a time period. The operations may further include determining a motion state of the subject in a motion cycle based on the image data; obtaining a physiological signal of the subject in the motion cycle; determining scan gating information of the subject based on the motion state of the subject and the physiological signal of the subject; and determining target image data of the subject based on the scan gating information.

In some embodiments, the image data may be acquired by the scanning device according to a fast acquisition sequence.

In some embodiments, the image data may include an image sequence. The image sequence may include multiple images arranged in time sequence. The operation of determining, based on the image data, a motion state of the subject in a motion cycle may include: identifying the subject in each of the multiple images using a trained machine learning model; and determining the motion state of the subject based on the identified subject.

In some embodiments, the image data may include an image sequence. The image sequence may include multiple images arranged in time sequence. The operation of determining, based on the image data, a motion state of the subject in a motion cycle may include: determining one or more characteristics of the subject in each of the multiple images; and determining the motion state of the subject based on the one or more characteristics of the subject.

In some embodiments, the one or more characteristics of the subject may include volume of the subject. The operation of determining the motion state of the subject based on the one or more characteristics of the subject may include: determining the motion state based on a change in the volume of the subject over time.

In some embodiments, the image data may include multiple image sequences acquired in multiple motion cycles, and the operation of determining, based on the image data, a motion state of the subject in a motion cycle may include: determining a target image sequence from the multiple image sequences; and determining, based on the target image sequence, the motion state of the subject in the motion cycle corresponding to the target image sequence.

In some embodiments, the operation of determining, based on the motion state of the subject and the physiological signal of the subject, scan gating information of the subject may include obtaining initial scan gating information based on the physiological signal; and obtaining the scan gating information of the subject by calibrating the initial scan gating information based on the motion state of the subject.

In some embodiments, the obtaining the scan gating information of the subject by calibrating the initial scan gating information based on the motion state of the subject may include: determining a correspondence relationship between the initial scan gating information and the motion state; and calibrating the initial scan gating information based on the correspondence relationship between the initial scan gating information and the motion state.

In some embodiments, the calibrating the initial scan gating information based on the correspondence relationship between the initial scan gating information and the motion state may include: determining a trigger threshold of the scan gating information based on the correspondence relationship between the initial scan gating information and the motion state; and calibrating the initial scan gating information based on the trigger threshold of the scan gating information.

In some embodiments, the determining, based on the motion state of the subject and the physiological signal of the subject, scan gating information of the subject may include: obtaining a trained machine learning model; and determining, based on the motion state of the subject and the physiological signal of the subject, the scan gating information of the subject using the trained machine learning model.

In some embodiments, the trained machine learning model may be obtained via a training process. The training process may include obtaining a plurality of training samples. Each of the training samples may include a motion state of a sample object and a physiological signal of the sample object deserved as an input in the training process and reference scan gating information deserved as an output in the training process. The training process may further include training a preliminary machine learning model based on the plurality of training samples.

In some embodiments, the physiological signal of the subject may include an electrocardiogram (ECG), a finger plethysmography, or a motion signal collected by a radar.

In some embodiments, the operation of determining, based on the scan gating information, target image data of the subject may include obtaining the target image data of the subject by triggering the scanning device to scan the subject according to the scan gating information.

In some embodiments, the operation of determining, based on the scan gating information, target image data of the subject may include obtaining initial image data of the subject by controlling the scanning device to scan the subject; and determining the target image data of the subject based on the scan gating information.

Another aspect of the present disclosure provides a system. The system may include at least one storage medium including a set of instructions; and at least one processor in communication with the at least one storage medium. When executing the set of instructions, the at least one processor may be directed to cause the system to perform operations including: obtaining image data of a subject, the image data being acquired by a scanning device scanning the subject during a time period; determining, based on the image data, a motion state of the subject in a motion cycle; obtaining a physiological signal of the subject in the motion cycle; determining, based on the motion state of the subject and the physiological signal of the subject, a correspondence relationship between the motion state and the physiological signal; calibrating the physiological signal of the subject based on the correspondence relationship; and obtaining target image data of the subject by triggering the scanning device to scan the subject based on the calibrated physiological signal.

Another aspect of the present disclosure provides a method. The method may be implemented on a computing apparatus, and the computing apparatus may include at least one processor and at least one storage device. The method may include obtaining image data of a subject. The image data may be acquired by a scanning device scanning the subject during a time period. The method may further include determining a motion state of the subject in a motion cycle based on the image data; obtaining a physiological signal of the subject in the motion cycle; determining scan gating information of the subject based on the motion state of the subject and the physiological signal of the subject; and determining target image data of the subject based on the scan gating information.

In some embodiments, the image data may be acquired by the scanning device according to a fast acquisition sequence.

In some embodiments, the image data may include an image sequence. The image sequence may include multiple images arranged in time sequence, and the operation of determining, based on the image data, a motion state of the subject in a motion cycle may include: identifying the subject in each of the multiple images using a trained machine learning model; and determining the motion state of the subject based on the identified subject.

In some embodiments, the image data may include an image sequence. The image sequence may include multiple images arranged in time sequence, and the operation of determining, based on the image data, a motion state of the subject in a motion cycle includes: determining one or more characteristics of the subject in each of the multiple images; and determining the motion state of the subject based on the one or more characteristics of the subject.

In some embodiments, the one or more characteristics of the subject may include volume of the subject, and the operation of determining the motion state of the subject based on the one or more characteristics of the subject may include: determining the motion state based on a change in the volume of the subject over time.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein.

DETAILED DESCRIPTION

Figure 1:
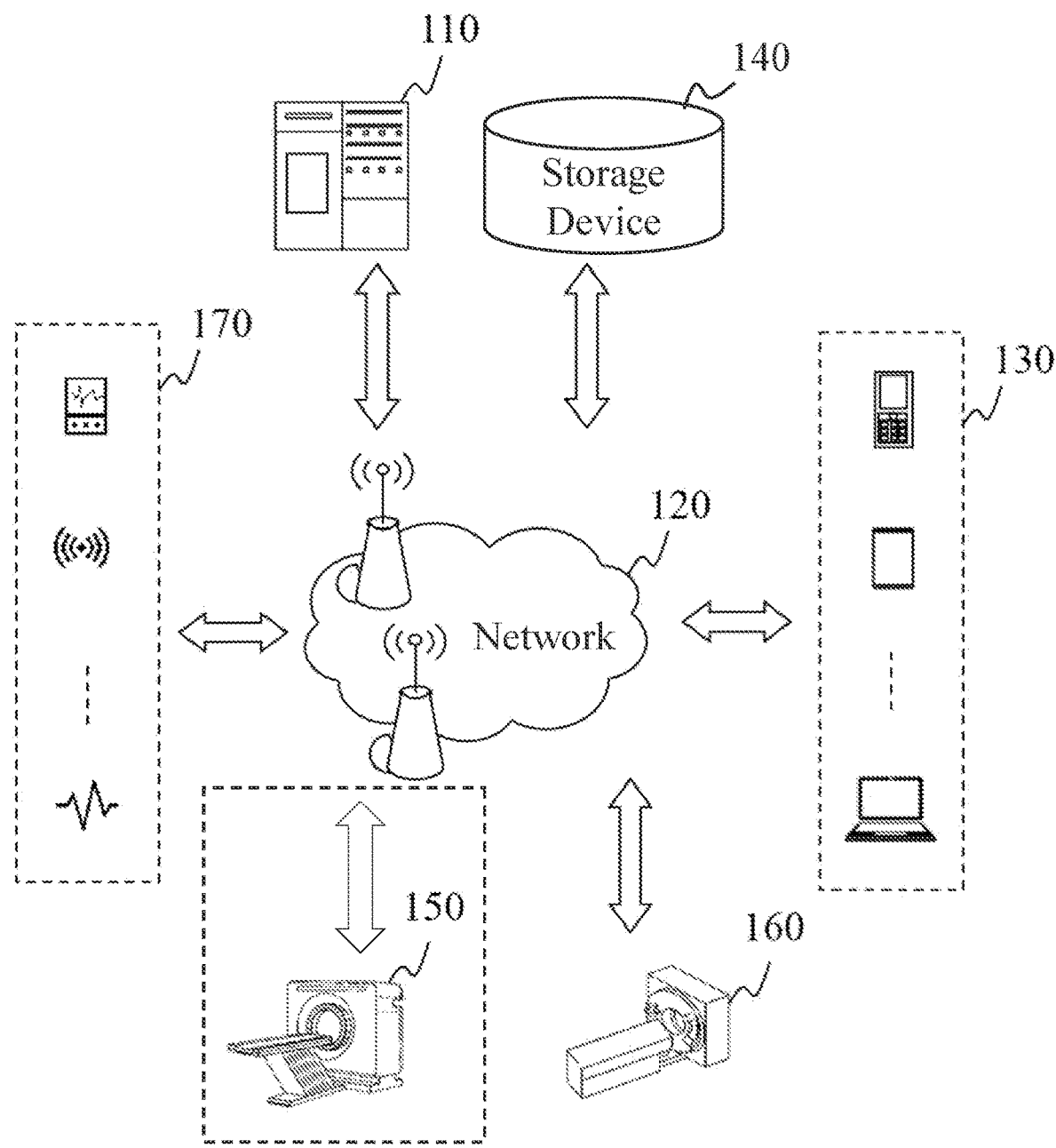
FIG. 1 is a schematic diagram illustrating an exemplary system for image scanning according to some embodiments of the present disclosure.

In order to illustrate the technical solutions related to the embodiments of the present disclosure, a brief introduction of the drawings referred to in the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

It will be understood that the terms "system," "device," "unit," and/or "module" used herein are one method to distinguish different components, elements, parts, sections, or assemblies of different levels in ascending order. However, the terms may be displaced by other expressions if they may achieve the same purpose.

As shown in the present disclosure and claims, unless the context clearly indicates exceptions, the words "a," "an," "one," and/or "the" do not specifically refer to the singular, but may also include the plural. The terms "including" and "comprising" only suggest that the steps and elements that have been clearly identified are included, and these steps and elements do not constitute an exclusive list, and the method or device may also include other steps or elements.

The flowcharts used in the present disclosure may illustrate operations executed by the system according to embodiments in the present disclosure. It should be understood that a previous operation or a subsequent operation of the flowcharts may not be accurately implemented in order. Conversely, various operations may be performed in inverted order, or simultaneously. Moreover, other operations may be added to the flowcharts, and one or more operations may be removed from the flowcharts.

FIG. 1 is a schematic diagram illustrating an exemplary system for image scanning according to some embodiments of the present disclosure.

As shown in FIG. 1, in some embodiments, the system 100 for image scanning (hereinafter referred to as the imaging system 100) may include a processing device 110, a network 120, a user terminal 130, a storage device 140, a scanning device 160, and a physiological signal acquisition device 170. The system 100 may obtain a target image of a subject by implementing a method and/or a process disclosed in the present disclosure.

The processing device 110 refers to a device used to process data and/or information from at least one component of the system 100 or an external data source (e.g., a cloud data center). The processing device 110 may access data or information from the user terminal 130, the storage device 140, and/or the scanning device 160 via the network 120. The processing device 110 may directly connect to the user terminal 130, the storage device 140, and/or the scanning device 160 to access information and/or data. The processing device 110 may process the obtained data and/or information. For example, the processing device 110 may determine a motion state of the subject in a motion cycle based on an image sequence; obtain a physiological signal of the subject in the motion cycle; determine scan gating information of the subject based on the motion state of the subject and the physiological signal of the subject. In some embodiments, the processing device 110 may be a single server or a group of servers. The processing device 110 may be local or remote. More information of the motion state, the physiological signal, and the scan gating information may be found elsewhere in the present disclosure, for example, FIG. 3 and the relevant descriptions.

The network 120 may connect various components of the system 100 and/or connect the system 100 with an external resource. In some embodiments, one or more components (e.g., the processing device 110, the user terminal 130, the storage device 140, and/or the scanning device 160) of system 100 may exchange information and/or data via network 120.

In some embodiments, the network 120 may be any wired or wireless network, or any combination thereof. In some embodiments, network 120 may include one or more network access points. For example, network 120 may include wired or wireless network access points, such as base stations and/or network switching points. Through the one or more network access points, the one or more components of the system 100 may be connected to network 120 to exchange data and/or information.

The user terminal 130 refers to one or more terminals or software used by a user (e.g., a caregiver, a doctor, etc.) of the system for image scanning. In some embodiments, the user terminal 130 may include, but may not be limited to, a smartphone, a tablet, a laptop, a desktop computer, etc. In some embodiments, the user terminal 130 may interact with other components in the system 100 via the network 120. For example, the user terminal 130 may send one or more control instructions to the processing device 110 to control the processing device 110 to determine the motion state of the subject in a motion cycle based on image data; obtain the physiological signal of the subject in a motion cycle; determine the scan gating information of the subject based on the motion state of the subject and the physiological signal of the subject.

The storage device 140 refers to a device used to store data, instructions, and/or any other information. In some embodiments, the storage device 140 may store data and/or information obtained from the user terminal 130, the storage device 140, and/or the scanning device 160. In some embodiments, the storage device 140 may include a large capacity memory, a removable memory, or any combination thereof.

The scanning device 160 refers to a device used to obtain a medical image and/or image data of a scanning site of the subject. The subject refers to an object that needs to be scanned. For example, the subject may be a patient, an experimenter, an animal, etc. The scanning site refers to a moveable part and/or a movable organ in the subject that need to be scanned. A motion may include a periodic motion (i.e., a flexible motion, such as a heartbeat, a breathing motion of the abdomen, etc.), a non-periodic motion (i.e., a rigid motion, such as a motion or a tremor of the head or limb), etc., of the subject. For example, the scanning site may be the heart, a liver, a lung, or any combination thereof. In some embodiments, the medical device 160 may scan the scanning site of the subject to obtain image data of the scanning site of the subject. In some embodiments, the scanning device 160 may scan the subject, obtain scanning data, and generate an image of the subject. In some embodiments, the scanning device 160 may be one device. For example, the scanning device 160 may be a positron emission tomography (PET) device, a single photon emission computed tomography (SPECT) device, a computed tomography (CT) device, or an MRI device, etc. Furthermore, the scanning device 160 may be a group of devices. For example, the scanning device 160 may include a PET device, an MRI device, and/or an SPECT device, or the like. In some embodiments, the scanning device 160 may include an angiography machine, such as a digital subtraction angiography (DSA).

The physiological signal acquisition device 170 refers to a device used to obtain a physiological signal of the subject. The physiological signal refers to a signal representing at least one physiological characteristics of the subject. The physiological characteristic refers to data related to the vital signs of the scanning object, such as electrocardiogram (ECG), pulse, etc. The physiological characteristic may include a motion characteristic or a motion situation of the scanning object. In some embodiments, the physiological signal acquisition device 170 may be a device that directly contacts the subject of the scanning object to obtain the physiological signal of the subject. Merely by way of example, the physiological signal acquisition device 170 may be an ECG machine used to obtain an ECG signal of the scanning object. As another example, the physiological signal acquisition device 170 may be a finger pulse acquisition device used to obtain a finger pulse of the scanning object. In some embodiments, the physiological acquisition device 170 may obtain the physiological signal of the subject through a non-direct contact. Merely by way of example, the physiological signal acquisition device 170 may include a radar device and/or an ultrasound device for obtaining the physiological signal of the subject.

It should be noted that the above descriptions are non-limiting. In some embodiments, the system 100 may also include an image acquisition device 150. The image acquisition device 150 refers to a device used to obtain image data of the scanning site of the subject. In some embodiments, the image acquisition device 150 may be a flat camera, such as a black and white camera, a color camera, a medical scanner, or any combination thereof. In some embodiments, the flat camera may capture a two-dimensional (2D) image of the subject. In some embodiments, the flat camera may include the black and white camera, the color camera, the scanner, or any combination thereof. In some embodiments, the image acquisition device 150 may include a three-dimensional (3D) camera, which may be directly used to obtain a depth image of the subject. For example, the image acquisition device 150 may be a structured light camera that can project specific light information (e.g., crisscross laser lines, black and white squares, circles, etc.) to the subject by a projector. For example, the image acquisition device 150 may be a binocular camera, a time of fit (TOF) camera, or the like. In some embodiments, the image acquisition device 150 may be a radar device for obtaining a radar image of the subject. In some embodiments, the image acquisition device 150 may be a medical image acquisition device, such as a magnetic resonance imaging (MRI) device, etc. In some embodiments, the system 100 may exclude the image acquisition device 150, and functions of the image acquisition device 150 may be implemented by the scanning device 160. In some embodiments, the image acquisition device 150 and the physiological signal acquisition device 170 may be integrated into one single device. In some embodiments, the system 100 may exclude the image acquisition device 150, and functions of the image acquisition device 150 may be implemented by the physiological signal acquisition device 170.

It should be noted that above description of the system 100 is merely provided for illustrative purposes, and may not be intended to limit the scope of the present disclosure. For those of ordinary skill in the art, various modifications or changes may be made based on the description in the present disclosure. For example, the system 100 may also include a database. However, these changes and modifications may not deviate from the scope of the present disclosure.

Figure 2:
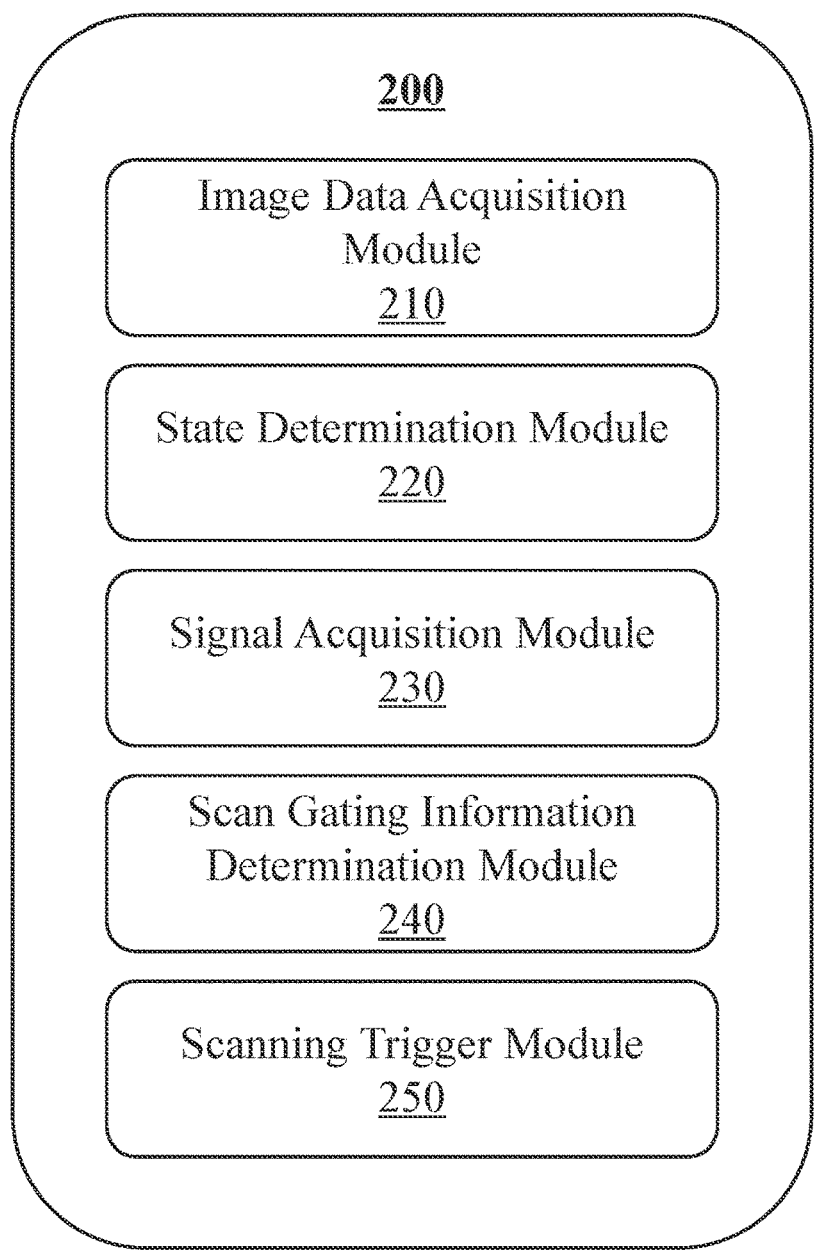
FIG. 2 is a block diagram illustrating an exemplary system for image scanning according to some embodiments of the present disclosure.

FIG. 2 is a block diagram illustrating an exemplary system 200 for image scanning according to some embodiments of the present disclosure. As shown in FIG. 2, the system 200 may include an image acquisition module 210, a state determination module 220, a signal acquisition module 230, a scan gating information determination module 240, and a scanning trigger module 250.

The image acquisition module 210 may be used to obtain image data of a subject. The image data may be acquired by a scanning device scans the subject during a time period. In some embodiments, the image data may include an image sequence including multiple images arranged in time sequence. Time intervals between any adjacent two images of the multiple images may be the same. A time interval between two adjacent images may be predetermined. For example, the time interval may be determined as 10 ms. In some embodiments, the image acquisition module 210 may also be used to identify the subject in each of the multiple images using a trained machine learning model (also referred to as a first trained machine learning model). For each of the multiple images, the motion state of the subject may be determined based on the identified subject. In some embodiments, the image acquisition module 210 may also be used to determine the target image data of the subject based on the scan gating information. More description of the image acquisition module 210 may be found elsewhere in the present disclosure, for example, FIG. 3 and the relevant description.

The state determination module 220 may be used to determine a motion state of the subject in a motion cycle based on the image data. In some embodiments, the state determination module 220 may be also used to determine one or more characteristics of the subject in each of the multiple images. The one or more characteristics of the subject may include volume of the subject. Thus, the state determination module 220 may further be used to determine the motion state based on a change in the volume of the subject over time. In some embodiments, the state determination module 220 may also be used to determine a target image sequence from the multiple image sequences, and determine the motion state of the subject in the motion cycle based on the target image sequence. More description of the state determination module 220 may be found elsewhere in the present disclosure, for example, FIG. 3 and the relevant description.

The signal acquisition module 230 may be used to obtain a physiological signal of the subject in the motion cycle. The physiological signal of the subject may include an ECG, a finger plethysmography, or a motion signal collected by a radar. More explanation of the signal acquisition module 230 may be found elsewhere in the present disclosure, for example, FIG. 3 and the relevant description.

The scan gating information determination module 240 may be used to determine scan gating information of the subject based on the motion state of the subject and the physiological signal of the subject.

The scanning trigger module 250 may be used to determine target image data of the subject based on the scan gating information. In some embodiments, the scanning trigger module 250 may also be used to obtain the target image data of the subject by triggering the scanning device to scan the subject according to the scan gating information. The triggering manners may include an ECG triggering, a finger plethysmography triggering, a non-contact triggering, and a radar triggering. More description of the scanning trigger module 250 may be found elsewhere in the present disclosure, for example, FIG. 3 and the relevant description.

In some embodiments, the scan gating information determination module 240 may further include a relationship determination unit. The relationship determination unit may be used to determine a correspondence relationship between the motion state of the subject and the physiological signal of the subject. More description of the relationship determination unit may be found elsewhere in the present disclosure, for example, FIG. 6 and the relevant description.

In some embodiments, the scan gating information determination module 240 may further include a signal calibration unit. The signal calibration unit may be used to calibrate the physiological signal based on the correspondence relationship between the motion state of the subject and the physiological signal of the subject. For more information on the signal calibration unit may be found elsewhere in the present disclosure, for example, FIG. 6 and the relevant description.

It should be noted that the above descriptions of the system for image scanning and modules thereof are merely provided for convenience, and may not limit the scope of the present disclosure. It can be understood that for those of ordinary skill in the art, after understanding the principle of the system, it is possible to arbitrarily combine various modules or connect sub-systems with other modules without deviating from this principle. In some embodiments, the image acquisition module 210, the state determination module 220, the signal acquisition module 230, the scan gating information determination module 240, the scanning trigger module 250, shown in FIG. 2 may be different modules in the same system, or may be one module that implements the functions of two or more modules mentioned above. For example, each module may share a common storage module, and each module may also have its own storage module. Such deformations are within the scope of the present disclosure.

Figure 3:
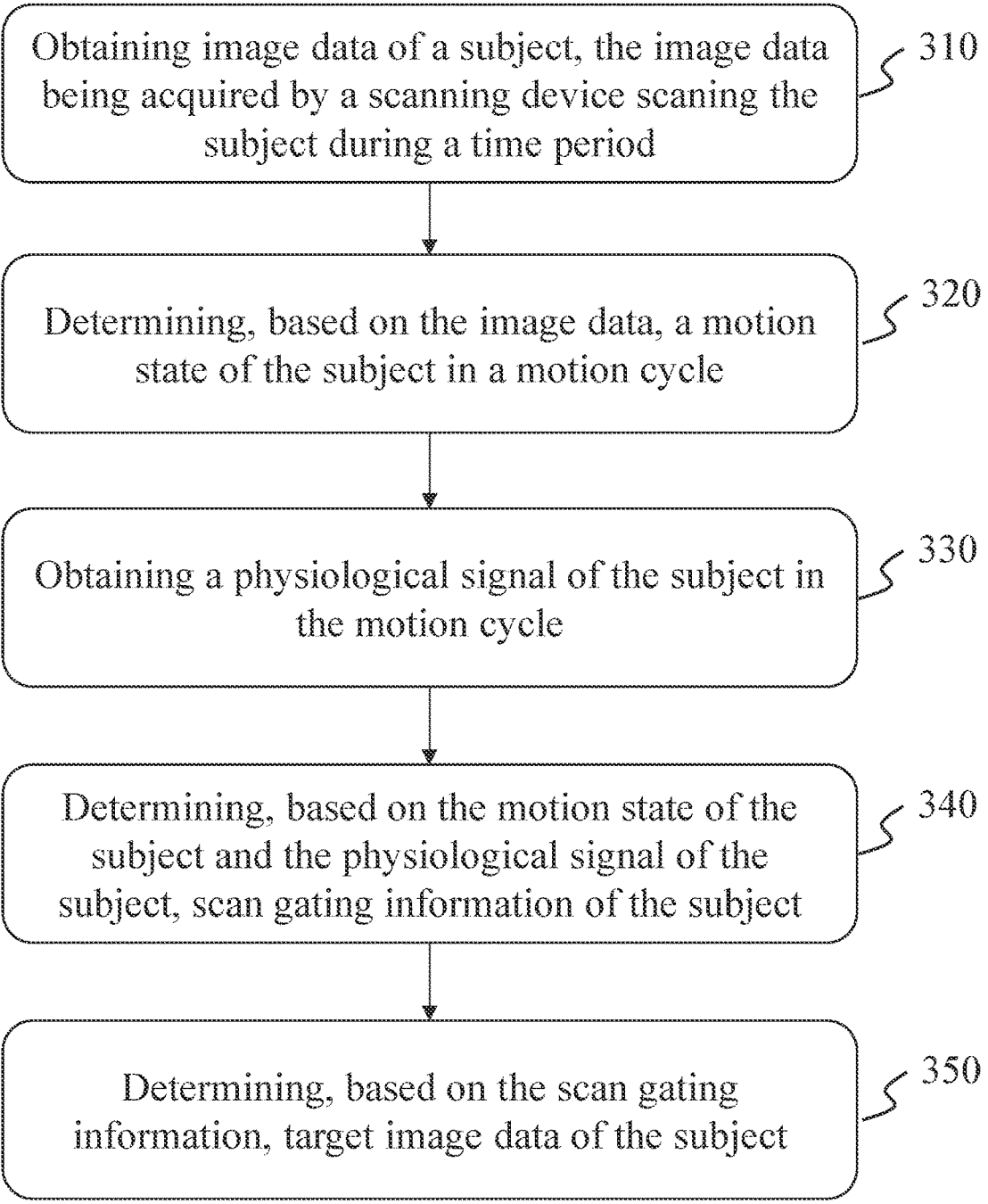
FIG. 3 is a flowchart illustrating an exemplary process for image scanning according to some embodiments of the present disclosure.

FIG. 3 is a flowchart illustrating an exemplary process for image scanning according to some embodiments of the present disclosure. As shown in FIG. 3, process 300 for image scanning may include following operations. In some embodiments, process 300 may be performed by the processing device 110 or the system 200.

In 310, image data of a subject may be obtained. In some embodiments, operation 310 may be performed by the image acquisition module 210 or the processing device 110.

The image data refers to imaging result data of a scanning site of the subject. The image data may be a two-dimensional (2D) image, a three-dimensional (3D) image, or a four-dimensional (4D) image. A format of the image data may be joint photographic experts group (JPEG), tagged image file format (TIFF), graphics interchange format (GIF), digital imaging and communications in medicine (DICOM), etc.

In some embodiments, the image data may include an image sequence, and the image sequence may include multiple images arranged in time sequence. In some embodiments, time intervals between any adjacent two images of the multiple images may be the same. For example, a time interval may be 20 ms. In some embodiments, time intervals between any adjacent two images of the multiple images may be different. More description of the subject may be found elsewhere in the present disclosure, for example, FIG. 1 and the relevant description.

In some embodiments, the image data may be acquired by a scanning device (e.g., the scanning device 160) scanning the subject during a time period. A duration of the time period may be determined by an operator of the scanning device, for example, 5 seconds.

In some embodiments, the image data may be acquired by the scanning device according to a fast acquisition sequence. Exemplary fast acquisition sequences may include a single shot fast spin echo (SSFSE) sequence, a Half-fourier acquisition single-shot fast spin echo sequence, etc. In some embodiments, the image data may be acquired by the scanning device according to a parallel acquisition technique.

In some embodiments, the image data may include multiple image sequences acquired in multiple motion cycles. One of the multiple image sequences may include multiple images of the subject acquired in a motion cycle arranged in time sequence. The motion cycle refers to a duration time that the subject completes a single motion, such as a duration time that the heart completes one heartbeat. As another example, the duration time that the scanning object completes one breath.

In some embodiments, the image acquisition module 210 may obtain multiple images of the subject at multiple time points in a motion cycle by the scanning device (e.g., the image acquisition device 150), and combine the multiple images of the subject obtained at the multiple time points in the motion cycle in an order of time sequence with image acquisition time to generate an image sequence within the corresponding motion cycle. In some embodiments, the image acquisition module 210 may obtain the multiple images of the subject acquired by the scanning device (e.g., image acquisition device 150) in multiple motion cycles, thereby generating the multiple image sequences acquired in the multiple motion cycles. The image acquisition module 210 may obtain the image data in one motion cycles from the multiple image sequences. More description of the image acquisition device 150 may be found elsewhere in the present disclosure, for example, FIG. 1 and the relevant description.

In some embodiments, the image acquisition module 210 may obtain initial image data of the subject within a preset time period. The initial image data may not only include the subject, for example, but also include other surrounding regions of the subject. The initial image data may include multiple initial images arranged in time sequence. The processing device 110 may obtain the image data by segmenting the initial image data. As used herein, the segmentation of the initial image may also be referred to identifying the subject from the initial image data. In some embodiments, the processing device 110 may obtain a segmentation model and segmenting the initial image data using the segmentation model. In some embodiments, the segmentation model may be a trained machine learning model, such as a deep neural network model, a convolution neural network model, a recurrent neural network model, a transformer model, etc. In some embodiments, the segmentation model may include using a region-based segmentation technique, a threshold-based segmentation technique, an edge-based segmentation technique, etc.

In some embodiments of the present disclosure, the identification processing performed on each of the multiple images may eliminate irrelevant information in the image, restore useful true information, enhance the detectability of relevant information, simplify data to the maximum extent, reduce the amount of data processing in subsequent processes, and make a physiological signal determined based on the image of the subject more accurate.

In 320, a motion state of the subject in a motion cycle may be determined based on the image data. In some embodiments, operation 320 may be performed by the state determination module 220 or the processing device 110.

The motion state may be denoted by or determined based on a change of a structure characteristics of the subject in a motion cycle. For example, the motion state may be denoted by a change in a volume, a thickness, a contour, a key point, etc., of the subject.

In some embodiments, the processing device 110 may determine one or more structure characteristics of the subject in each of the multiple images, and determine the motion state of the subject based on the one or more structure characteristics of the subject. Merely by way of example, for each of the multiple images, the state determination module 220 may perform an image recognition on the image to obtain the one or more structure characteristics of the subject in the image, and then sort the one or more structure characteristics in an order of time sequence to obtain the change of the one or more structure characteristics over time. Thus, the motion state in the motion cycle may be denoted by or determined based on the change of the one or more characteristics over time. The image recognition performed on the image may extract the one or more structure characteristics of the subject based on a histogram of oriented gradients (HOG) feature, a local binary patterns (LBP) feature, a Haar-like feature, or other algorithms.

For example, the motion state of the subject may include a position change of the subject over time. The processing device 110 may determine the position change of the subject based on the change of a structure characteristics over time. As a further example, the processing device 110 may determine a position change of the contour of the subject over time. The processing device 110 may designate the position change of the contour of the subject as the position change of the subject.

In some embodiments, the one or more structure characteristics of the subject may include the volume of the subject.

In some embodiments, the state determination module 220 may determine volumes of the subject in the multiple images. Based on the volumes of the subject in the multiple images, a change in the volume of the subject in the motion cycle may be determined. The state determination module 220 may determine the motion state of the subject based on the change in the volume of the subject over time.

Figure 5:
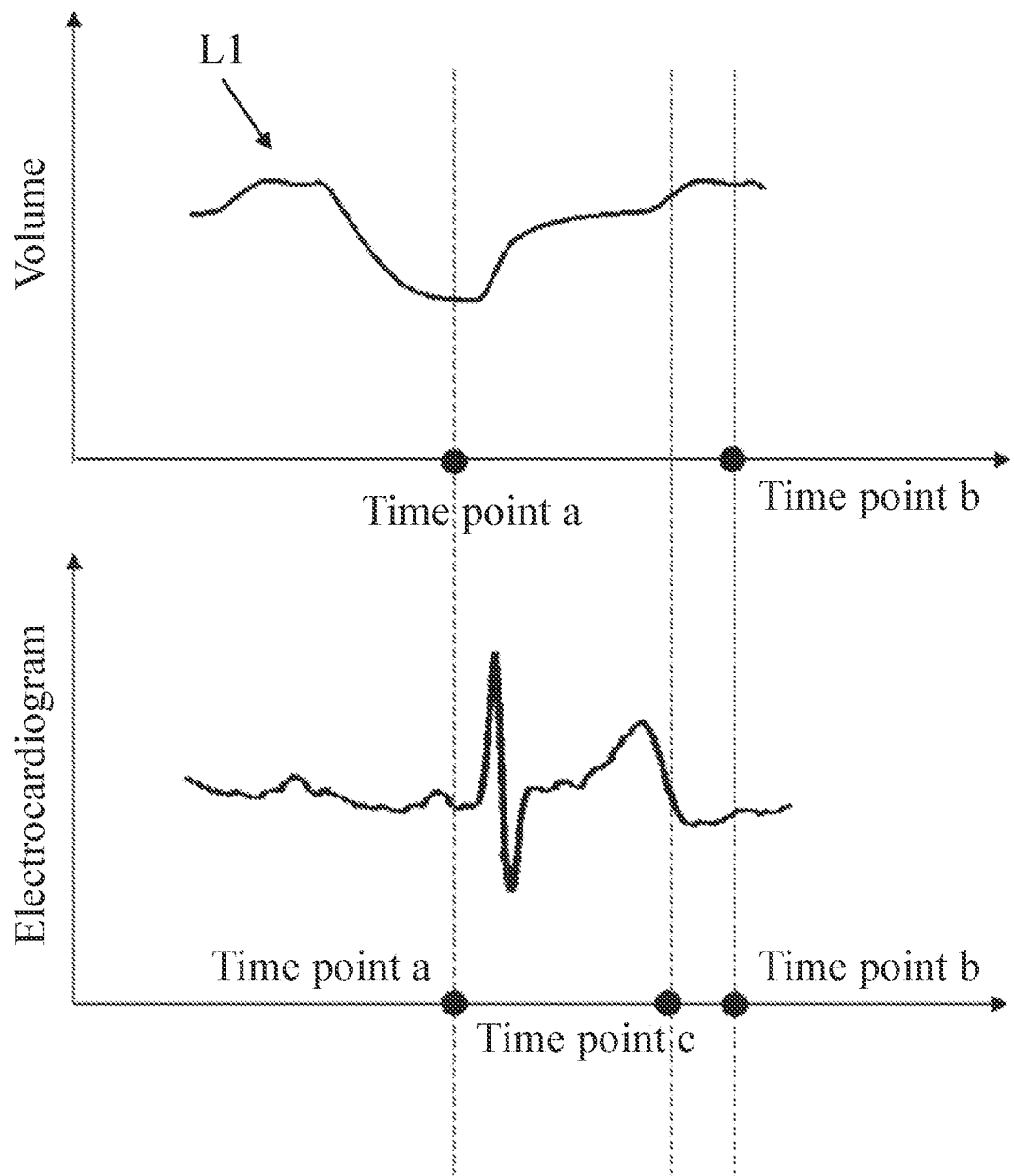
FIG. 5 is a schematic diagram illustrating an exemplary correlation between a volume of the heart and a corresponding electrocardiogram in a motion cycle of the subject according to some embodiments of the present disclosure.

FIG. 5 is a schematic diagram illustrating an exemplary correlation between a volume of the heart and a corresponding electrocardiogram in a motion cycle of the subject according to some embodiments of the present disclosure. Taking the subject as the heart of a person as an example, the image acquisition module 210 may obtain image data of the heart by an MRI device. The state determination module 220 may identify the heart in multiple images of the image data based on a heart segmentation algorithm, and then determine volumes of the heart in the multiple images of the heart. The state determination module 220 may sort the volumes of the heart in the time sequence, thereby obtaining a curve of the change in the volume of the heart over time. The volumes of the heart in a motion cycle may be determined from the curve L1 as shown in FIG. 5. The heart segmentation algorithm may include identifying the heart based on an image feature (e.g., a grayscale threshold, a region growth, or edges), or identifying the heart based on a prior model (e.g., a deformable model, a statistical model, etc.).

It can be understood that during the motion of the subject, the volume of the subject may change significantly with the motion. Therefore, based on the volumes of the subject in the multiple images, the change in the volume of the subject over time in a motion cycle may be determined, thus the motion of the subject in the motion cycle may be represented more accurately and clearly.

In some embodiments, the image data obtained in operation 310 may include multiple image sequences acquired in multiple motion cycles. The state determination module 220 may filter the multiple image sequences acquired in the multiple motion cycles to determine a target image sequence, and determine the motion state of the subject in the motion cycle corresponding to the target image sequence based on the target image sequence. The target image sequence refers to an image sequence better representing the motion of the subject than other image sequences in the multiple image sequences. In some embodiments, the target image sequence better representing the motion of subject may be an image sequence obtained by the image acquisition module 210 in a motion cycle with a normal motion of the subject. In some embodiments, the target image sequence may be an image sequence with higher image quality (e.g., the highest clarity degree) among the multiple image sequences. As used herein, the normal motion of the subject refers to that the motion of the subject represented in the image sequence satisfies a condition (e.g., the motion law of the type of the subject). For example, the normal motion in a motion cycle of the subject refers to a duration time of the motion cycle of the subject being within a normal range. As another example, the normal motion in a motion cycle of the subject refers to a motion amplitude or motion intensity of the motion cycle of the subject being within a normal range. As a further example, taking the heart as the subject, a beating cycle with a normal beat of the heart is within a range of 0.6 s-1 s. If the duration time of the heart beating is within the range of 0.6 s-1 s (e.g., 0.8 s), the motion of the heart may be considered as normal in the motion cycle.

In some embodiments, the state determination module 220 may determine the target image sequence based on a time sequence of obtaining the multiple image sequences. For example, the state determination module 220 may designate an image sequence that is located in a middle position among the multiple image sequences in the time sequence as the target image sequence. Merely by way of example, if the image acquisition module 210 obtains an image sequence in a motion cycle A, an image sequence in a motion cycle B, an image sequence in a motion cycle C, and an image sequence in a motion cycle D in time sequence, then the signal determination module 220 may designate the image sequence in the motion cycle B or the image sequence in the motion cycle C as the target image sequence. In some embodiments, the state determination module 220 may determine an average image sequence of the multiple image sequences, and designate the average image sequence as the target image sequence. In some embodiments, the state determination module 220 may determine each image in the average image sequence by averaging multiple images in the multiple image sequences at each time point in the motion cycle. For example, the state determination module 220 may average multiple first images at a same first time point of multiple image sequences to obtain an average result of the multiple first images, and average multiple second images at a same second time point of multiple image sequences to obtain an average result of the multiple second images, and so on, until all the images included in the multiple image sequences are averaged, and all the average results may form the average image sequence, which may be designated as the target image sequence.

In some embodiments, the state determination module 220 may determine the motion state of the subject in the motion cycle based on the target image sequence.

In some embodiments of the present disclosure, by filtering the multiple image sequences of the subject in the multiple motion cycles, the target image sequence better representing the motion of the subject may be determined, thereby making the physiological signal of the subject in one motion cycle more accurate based on the target image sequence, and more in line with the actual motion of the subject.

In some embodiments, for each of the multiple images, the image acquisition module 210 may identify the subject in each of the multiple images using a trained machine learning model (also referred to as a first trained machine learning model). Then, the state determination module 220 may determine the motion state of the subject based on the identified subject. More description of the embodiment may be found elsewhere in the present disclosure, for example, FIG. 4 and the relevant description.

In 330, a physiological signal of the subject in the motion cycle may be obtained. In some embodiments, operation 330 may be performed by the signal acquisition module 230 or the processing device 110. In some embodiments, the physiological signal and the image data obtained in operation 310 may be respectively acquired by the physiological signal acquisition device 170 and the image acquisition device 150 simultaneously.

The physiological signal refers to a signal that represents one or more physiological characteristics (e.g., an ECG, a pulse, etc.) of the subject. The physiological signal may include a physiological characteristic curve such as a respiratory curve, an ECG curve, a finger plethysmography curve, etc.

In some embodiments, the signal acquisition module 230 may obtain the physiological signal of the subject at multiple time points by the physiological signal acquisition device 170, and determine the physiological signal of the subject in the motion cycle. For example, if the subject is the heart of a person, the signal acquisition module 230 may obtain the ECG of the heart during a process of completing a heartbeat by an ECG machine. As another example, if the subject is a lung of a person, and the signal acquisition module 230 may obtain a radar signal from the lung at multiple time points during the process of completing a breath by a radar device.

In some embodiments, for each of different subjects, the physiological signal of the subject may be processed to determine the scanning time of the scanning device (e.g., the scanning device 160), thereby determining the scan gating information of the subject. For example, a steady-state period and a data acquisition period in a motion cycle of the subject may be determined based on the physiological signal. The steady-state period refers to a time period without performing a scan, that is, a non-data acquisition period. The data acquisition period is a time period with performing a scan. The operation performed by the scanning device 160 during the steady-state period of the subject and during the data acquisition period of the subject may be different.

In some embodiments, the physiological signal of the subject may include an ECG, a finger plethysmography, a radar signal collected by a radar (also referred to as a motion signal collected by a radar), or the like. The radar signal may include a motion signal of the subject acquired when the subject is moving, such as a signal representing the breathing motion of the abdomen of person or the limb motion of the person.

In 340, scan gating information of the subject may be determined based on the motion state of the subject and the physiological signal of the subject. In some embodiments, operation 340 may be performed by the scan gating information determination module 240 or the processing device 110.

The scan gating information refers to information used to control a scanning device (e.g., the scanning device 160) to scan the subject or used to determine target scanning data from initial scanning data. In some embodiments, the scan gating information may be denoted as a scan gating curve. In some embodiments, the scan gating information may be denoted as a corresponding relationship (e.g., a table) between time and values The time may include multiple time points within a process of controlling the scanning device (e.g., the medical device 160) to perform the scanning operation, and the value may be an information value of the scan gating information corresponding to one of the multiple time points, such as a voltage value, etc.

In some embodiments, the scan gating information determination module 240 may determine the scan gating information of the subject based on the motion state of the subject in the motion cycle and the physiological signal of the subject in the motion cycle.

The motion cycle may be composed of multiple time points, and there may be a correspondence relationship between a physiological signal acquired at each of the multiple time points in the motion cycle and the motion state at the corresponding time point.

In some embodiments, the scan gating information determination module 240 may determine a trigger threshold of the scan gating information based on the correspondence relationship between the motion state of the subject and the physiological signal of the subject. The physiological signal may represent the physiological characteristic (e.g., motion) of the subject over time. For example, the physiological signal may record a change of voltage over time. The change of voltage over time may represent the motion of the subject. The trigger threshold may be a value (e.g., a voltage value) (also referred to as scan gating signal) for data acquisition (e.g., triggering a scanning device to scan the subject) in the physiological signal (or scan gating information) acquired in the motion cycle of the subject. In some embodiments, the motion of the subject below the trigger threshold may be relatively slow (e.g., an end stage of exhalation in a respiratory motion).

In some embodiments, the scan gating information determination module 240 may determine a portion (also referred to as a target physiological signal) of the physiological signal in the motion cycle corresponding to a slow motion of the subject based on the motion state of the subject in a motion cycle. Based on a time point corresponding to the target physiological signal, the scan gating signal (i.e., the trigger threshold) corresponding to the target physiological signal may be determined. The scan gating signal may be designated as the trigger threshold of the scan gating information. Taking the subject as the heart of a person as an example, the scan gating information determination module 240 may determine time points corresponding to the end stage of the cardiac contraction phase and the end stage of the cardiac diastolic phase based on the change in volume of the heart in the motion cycle, thereby determining an electric potential (i.e., a voltage value) corresponding to the end stage of cardiac contraction phase and an electric potential corresponding to the end stage of the cardiac diastolic phase. In some embodiments, the scan gating information determination module 240 may designate the electric potential corresponding to the end stage of the cardiac contraction phase and the electric potential corresponding to the end stage of the cardiac diastolic phase as the trigger thresholds to generate a corresponding scan gating curve. In some embodiments, in the scan gating curve, except for the time points corresponding to the end stage of cardiac contraction phase and the end stage of the cardiac diastolic phase, electric potentials corresponding to other time points may be less than the trigger thresholds. In some embodiments, in the scan gating curve, a time period between the time points corresponding to the end stage of cardiac contraction phase and the end stage of the cardiac diastolic phase may be for data acquisition; and other time periods may be not for data acquisition.

In some embodiments, the scan gating information determination module 240 may designate one of the electric potential corresponding to the end stage of the cardiac contraction phase and the electric potential corresponding to the end stage of the cardiac diastolic phase as the trigger thresholds to generate a corresponding scan gating curve. For example, the larger one of the electric potential corresponding to the end stage of the cardiac contraction phase and the electric potential corresponding to the end stage of the cardiac diastolic phase may be designated as the trigger threshold. In some embodiments, in the scan gating curve, a time period between the time points corresponding to two trigger thresholds in two adjacent motion cycles may be for data acquisition; and other time periods may be not for data acquisition.

In some embodiments, the scan gating information determination module 240 may determine the scan gating information of the subject based on a correspondence relationship between the motion state of the subject and the physiological signal of the subject. For example, the scan gating information determination module 240 may determine the trigger threshold based on the correspondence relationship between the motion state of the subject and the physiological signal of the subject. The scan gating information determination module 240 may determine the correspondence relationship between the motion state of the subject and the physiological signal of the subject based on the time points in the motion cycle. The scan gating information determination module

240 may determine target motion information from the motion state and the target motion information may satisfy a condition. The scan gating information determination module 240 may determine one or more time points corresponding to the target motion information and determine the trigger threshold from the physiological signal of the subject based on the one or more time points corresponding to the target motion information. The target motion information satisfying the condition may refer to that the motion speed, the motion acceleration, the motion amplitude, and/or the motion intensity at the one or more time points corresponding to the target motion information are less than a threshold. As described elsewhere, the motion state may be denoted by the volume change, the position change of the contour, the thickness, the position change of the key point, etc., of the subject over time. The target motion information may be such that the volume change, the position change of the contour, the thickness change, the position change of the key point, etc., of the subject over time satisfy a condition (e.g., the change size being less than a threshold or greater than a threshold).

Taking the image data of the subject including an image of the end stage of cardiac contraction phase and an image of the end stage of the cardiac diastolic phase, and the physiological signal being the ECG as an example, the scan gating information determination module 240 may use an ECG voltage at a time point (referred to as the first time point) with a volume of the heart (or the volume change) being the smallest, and an ECG voltage at a time point (referred to as the second time point) with a volume of the heart tending to the maximum as a first trigger threshold and a second trigger threshold, respectively. For generating the scan gating curve, values corresponding to the first time point and the second time point may be designated as the first trigger threshold and the second trigger threshold in the scan gating curve, respectively. The values corresponding to other time points in the curve may be designated as values less than the first trigger threshold, and less than the second trigger threshold to obtain the scan gating curve. A first time period after the first time point and a second time period after the second time point may be the data acquisition period, and other time periods may the steady-state periods. The length of the first time period and/or the second time period may be preset by an operator. For example, the first time period may be designated as 100 ms. In some embodiments, a time period between the first time point and the second time point may be for data acquisition period.

In some embodiments, the scan gating curve may be a 0-1 curve, where the values corresponding to the first time period and the second time period or the timer period between the first time point and the second time point are set to 1, and values corresponding to other time points are set to 0. When a value corresponding to a time point in the scan gating curve is 1, the scanning device (e.g., the scanning device 160) may be triggered to apply an imaging sequence in the first time period and the second time period to obtain the MR signal of the subject for imaging. When a value corresponding to a time point in the scan gating curve is 0, the scanning device (e.g., the scanning device 160) is triggered to apply a steady-state sequence without the need for imaging.

In some embodiments, the scan gating information determination module 240 may obtain initial scan gating information based on the physiological signal, and obtain the scan gating information of the subject by calibrating the initial scan gating information based on the motion state of the subject.

For example, taking the physiological signal as the ECG as an example, usually (applicable to most people), a QRS wave complex of the ECG is a cardiac contraction phase, and a subsequent 500 ms delay of the QRS wave complex is a cardiac diastolic phase, and a duration of the cardiac diastolic phase is usually 0.4 s. Based on this situation, an electric potential of a time point (a time point c shown in FIG. 5) with a subsequent 900 ms delay of the QRS wave complex may be designated as the trigger threshold in the initial scan gating information to trigger the scanning device (e.g., the scanning device 160) to scan the subject. The initial scan gating information may be preset based on a type of the physiological signal (e.g., ECG, motion signal, etc.) and medical rules (e.g., the QRS wave complex of the ECG being the cardiac contraction phase, and a subsequent 500 ms delay of the QRS wave complex being the cardiac diastolic phase, and a duration of the cardiac diastolic phase being usually 0.4 s, etc.).

Data may be collected for the ECG curve after a time delay (TD, time delay) after a R-wave of the ECG curve is triggered. A required time length for collecting specific data is a collection window. A position of the collection window may be a data acquisition period, and other positions may be steady-state periods.

Taking the physiological signal as a respiratory curve as an example, the collection window may be arranged at an end stage of an exhalation in a respiratory motion. The position of the collection window is the data collection period of the respiratory curve, and other positions are the steady-state periods. When a real-time physiological signal curve of the subject is in the data collection period, the scanning device (e.g., the scanning device 160) may apply an imaging sequence to obtain a magnetic resonance (MR) signal of the subject. The imaging sequence may include a position encoding gradient and a second scattered phase gradient. When the real-time physiological signal curve of the subject is in a steady-state period, the scanning device (e.g., the scanning device 160) may apply a steady-state sequence. Since imaging is not required, the steady-state sequence may merely include a first scattered phase gradient to maintain the coherence of the imaging sequence. During processing of an MRI scanning, there may be a lot of noise. A great amount of noise may affect the comfort of a scanning object (e.g., a patient), thereby affecting the breathing state of the scanning object. An unstable breathing state may affect the stability of the gating triggering, the image acquisition efficiency, and make the breathing waveform in the collection window inconsistent. The inconsistent breathing waveform may be more likely to cause breathing artifacts. Applying a steady-state sequence during the steady-state period may reduce an amplitude of a scanning sound during the steady-state period and give the scanning sound a sense of rhythm, guiding the scanning object to breathe smoothly without collecting an MR signal. More description of the physiological signal and the physiological signal acquisition device 170 may be found elsewhere in the present disclosure, for example, FIG. 1 and the relevant description.

In some embodiments, the scan gating information determination module 240 may determine a correspondence relationship between the initial scan gating information and the motion state of the subject in the motion cycle, and calibrate the initial scan gating information based on the correspondence relationship between the initial scan gating information and the motion state.

In some embodiments, the scan gating information determination module 240 may determine the trigger threshold of the scan gating information based on the correspondence relationship between the initial scan gating information and the motion state, and calibrate the initial scan gating information based on the trigger threshold of the scan gating information. For example, taking the image data of the subject including an image of the end stage of cardiac contraction phase, and the physiological signal being the ECG as an example, based on the correspondence relationship between the initial scan gating information and the motion state, the scan gating information determination module 240 may obtain a time point corresponding to the end stage of cardiac contraction phase and an ECG potential of the time point, and determine the ECG potential as the trigger threshold. For the initial scanning gate information, the ECG potential of the time point may be used to calibrate the trigger threshold of the initial scan gating information and obtain the scan gating information. For example, the trigger threshold for the initial scan gating information may be replaced by the ECG potential of the time point. In other words, the time period for data acquisition in the initial scan gating information may be adjusted based on the ECG potential of the time point In some embodiments, the scan gating information determination module 240 may obtain a trained machine learning model (also referred to as a second trained machine learning model), and determine the scan gating information of the subject using the trained machine learning model based on the motion state of the subject and the physiological signal of the subject.

The second trained machine learning model may be a machine learning model used to determine the scan gating information of the subject by processing the motion state (or image data) of the subject and physiological signal of the subject. In some embodiments, the trained machine learning model may be constructed based on a deep neural network (DNN) model. The DNN model may include a convolutional neural network (CNN) model, a recurrent neural network (RNN) model, or the like. An input of the trained machine learning model may include the motion state (or image data) of the subject and the physiological signal of the subject, and an output of the trained machine learning model may include the scan gating information of the subject. An input of the trained machine learning model may include the motion state (or image data) of the subject and the physiological signal of the subject, and an output of the trained machine learning model may include the scan gating information of the subject.

In some embodiments, the trained machine learning model may be implemented on one or more devices (e.g., the processing device 110) and/or modules (e.g., the scan gating information determination module 240). For example, one or more components of the trained machine learning model may be implemented on the same processing device (e.g., the processing device 110). In some embodiments, at least two processing devices may perform parallel processing operations in the trained machine learning model, for example, assigning cores of two or more processing device to operations of different nodes (e.g., cores, pooling nodes, neurons) of the trained machine learning model. For example, a first graphics processing unit (GPU) of the processing device may perform operations corresponding to core A and core B, while a second core of the processing device may perform operations corresponding to core C and core D. Similarly, at least two GPUs of the processing device may also perform operations corresponding to other nodes (e.g., cores, pooling nodes, neurons) of the trained machine learning model.

In some embodiments, the storage device (e.g., the storage device 140) may be used to store data related to the trained machine learning model. The data related to the trained machine learning model may include an activation function, a learning authority of a pooled node, and/or a network topology (e.g., a type of each processing layer of the trained machine learning model, etc.). Optionally, the storage device (e.g., the storage device 140) may also store a training dataset and/or a validation dataset. The training dataset may be used to train a preliminary machine learning model, and may include sample physiological signals and sample motion states of the subject with labels. The validation dataset may be used to validate the trained machine learning model.

In some embodiments, a training system of the trained machine learning model (hereinafter referred to as the training system) may obtain a plurality of training samples. Each of the training samples may include a motion state of a sample object and a physiological signal of the sample object deserved as an input in a training process of the trained machine learning model, and a reference scan gating information deserved as an output in the training process. The training system may also train a preliminary machine learning model based on the plurality of training samples.

In some embodiments, the training system may use a training dataset (a sample set composed of the plurality of training samples) to train the preliminary machine learning model, in order to determine a plurality of training values of parameters of the preliminary machine learning model. In other words, the training system may train a neural network of the trained machine learning model to update a plurality of initial training values of the parameters of the neutral network from a plurality of initial values to the plurality of training values to obtain the trained machine learning model.

In some embodiments, the training process of the trained machine learning model may be an offline process. During the training process, a training dataset with real value labels (i.e., a corresponding scan gating information set corresponding to the training dataset) may be assembled. For example, a training dataset with multiple subjects may be constructed. In the training dataset, each sample may include a motion state of a sample object and a physiological signal of the sample object. In the training process, a mapping between characteristics and true values may be learned or trained by minimizing a best fit between a predicted value (predicted scan gating information) and a true value (reasonable scan gating information corresponding to the physiological signal of the sample object and the motion state of the sample object) on a portion or the whole of the training dataset.

In some embodiments, the training system may update the parameters by performing iterations of a backpropagation neural network training process (e.g., a random gradient descent backpropagation training technique) to determine updated parameters of the neural network. That is, the training system may backpropagation an error determined based on the output of the preliminary machine learning model to the neural network, in order to adjust the parameters of the neural network.

During the training process, the neural network of the preliminary machine learning model may process the training dataset with labels. Thus, the neural network may learn how to provide output for new input data by generalizing the information learned during the training process from the training data. In some embodiments, after the learning is completed, the validation dataset may be processed by the neural network to validate a learning result.

In some embodiments, a processing device (e.g., the processing device 110) may determine whether a termination condition is met in an iteration. For example, the termination condition may be that a value of a cost function in the iteration is less than a threshold (e.g., a minimum cost function Jmin). Other termination conditions may include a count of iterations reaching a maximum number (or count), an approximation error being less than a certain threshold, a difference between a value of a cost function obtained in a previous iteration and a value of a cost function obtained in a current iteration (or differences between values of cost function of a certain counts or consecutive iterations) less than a certain threshold, a difference between an approximate error of the previous iteration and an approximate error of the current iteration (or differences between approximate errors of a certain counts or consecutive iterations) being less than a certain threshold. In response to not meeting the termination condition in an iteration, a further iteration may be performed until the termination condition is met. In response to meeting the termination condition in the current iteration, the iteration process may be terminated and the trained machine learning model may be stored and/or output. The trained machine learning model generated by the training process may be stored in the memory of the processing device (e.g., the processing device 110), memory, or a storage device (e.g., the storage device 140), or the scan gating information determination module 240.

In some embodiments, the plurality of labeled training samples may include labels (e.g., labels indicating a result of a given action or an event, such as a reasonable scan gating information for the subject), which may be manually set to label the training dataset with a reasonable scan gating information to obtain the plurality of labeled training samples.

In some embodiments, the training system may collect the training data (i.e., the physiological signal of the sample object and motion state of the sample object) from one or more storage devices (e.g., the storage device 140) and/or modules (e.g., the state determination module 220, the signal acquisition module 230). The collected data may be stored and/or transmitted to a buffer, memory, cache, processor, and/or another device used for model training. The collected training data may be input into a machine learning algorithm. In some embodiments, the reference scan gating information may be determined based on the sample motion state and the sample physiological signal according to process 300 or process 600 as described in the present disclosure.

Taking FIG. 5 as an example, if the trigger threshold is not determined based on above methods, the trigger threshold may be designated as a default value. For example, a QRS wave complex in the ECG is usually considered as a cardiac contraction phase, and a subsequent 500 ms delay of the QRS wave complex is usually considered as a cardiac diastolic phase with a duration of 0.4 s. A scanning device (e.g., the scanning device 160) may be triggered at a time point (e.g., a time point c shown in FIG. 5) with a subsequent 900 ms delay of the QRS wave complex to obtain an image of the heart. However, due to the variable conditions of patients, motion modes of heart of different patients may also vary, thus the trigger threshold with the default value may not suitable for every patient. For example, a heart of a normal person usually begins to contract after the QRS wave complex arrives. However, the heart of a patient may start to contract after a certain time period of the QRS wave complex. For the patient, if a scanning operation is directly triggered during the QRS wave complex, an image obtained by the scanning operation may include a lot of artifacts. For example, at the time point c shown in FIG. 5, the heart of the heart patient is still in the cardiac contraction phase, and the image obtained by triggering the scanning device to scan the heart at the time point c may include a lot of artifacts.

In order to achieve a precise scanning trigger for different subjects, when determining the scan gating information, the scan gating information determination module 240 may use a cardiac voltage corresponding to the time point a or a cardiac voltage corresponding to the time point b shown in FIG. 5 as the trigger threshold. When the cardiac voltage of the subject is the cardiac voltage corresponding to the time point a or the cardiac voltage corresponding to the time point b, the scanning device (e.g., the scanning device 160) may triggered to scan the subject, to obtain an image of the subject.

It can be understood that the scan gating information may be multiple types (e.g., ECG, finger plethysmography, a motion of the subject, etc.), therefore, a type of the trigger threshold of the scan gating information determined by the scan gating information determination module 240 may be different. For example, when the scan gating information is ECG, the trigger threshold of the scan gating information may be a potential corresponding to a slow motion of the subject (e.g., the potential corresponding to the end stage of cardiac contraction phase, or the end stage of the cardiac diastolic phase). When the scan gating information is a motion of the subject collected by a radar, the trigger threshold of the scan gating information may be a corresponding motion signal (also referred to as a motion signal threshold) collected by the radar when the motion of the subject is relatively slow. When the scan gating signal is a finger plethysmography, the trigger threshold of the scan gating information may be a corresponding finger plethysmography amplitude (also referred to as a finger plethysmography amplitude threshold) when the motion of the subject is relatively slow.

In some embodiments of the present disclosure, the trigger threshold of the scan gating information may be determined based on the correspondence relationship between the initial scan gating information and the motion state to achieve a precise control of scanning trigger. Thus, when a scanning device is triggered to scan the subject, the subject may be in a relatively smooth motion state, resulting in less artifacts and higher image quality of an image of the subject.

In 350, target image data of the subject may be determined based on the scan gating information. In some embodiments, operation 350 may be performed by the image data acquisition module 210, the scanning trigger module 250, or another image data acquisition module.

In some embodiments, the target image data may include an image of the subject. In some embodiments, the target image data refers to scanning data (e.g., K-space data, projection data, etc.) of the subject.

In some embodiments, the scanning trigger module 250 may obtain the target image data of the subject by triggering the scanning device to scan the subject according to the scan gating information.

In some embodiments, the scanning trigger module 250 may read the trigger threshold based on the scan gating information determined by the scan gating information determination module 240, and then control the scanning device (e.g., the scanning device 160) to scan the subject to generate the image of the subject. For example, when an electric potential of the heart obtained by the ECG machine is the electric potential corresponding to the end stage of cardiac contraction phase, the scanning trigger module 250 may control the CT device to scan the heart and generate a CT image of the heart.

In some embodiments, the scanning trigger module 250 may trigger the scanning device to scan the subject according to the scan gating information by at least one of a ECG triggering, a finger plethysmography triggering, and motion signal triggering. For example, when a real-time cardiac voltage is the electric potential corresponding to the end stage of cardiac contraction phase or the end stage of the cardiac diastolic phase, the scanning trigger module 250 may control the scanning device (e.g., medical scanning device 160) to scan the subject to obtain target image data of the subject. When the real-time motion signal collected by the radar is within the motion signal threshold, the scanning trigger module 250 may control the scanning device (e.g., the scanning device 160) to scan the subject to obtain the target image data of the subject. When the real-time finger plethysmography amplitude is within a finger plethysmography amplitude threshold, the scanning trigger module 250 may control the scanning device (e.g., the scanning device 160) to scan the subject to obtain the target image data of the subject.

In some embodiments, the motion state of the subject in the motion cycle may be determined based on the image data of the subject acquired during a time period; the physiological signal of the subject in the motion cycle may be obtained; based on the motion state of the subject and the physiological signal of the subject, the scan gating information of the subject may be determined; based on the scan gating information, the target image data of the subject may be determined. It can be understood that different subjects have different motion modes. For example, the heart of a normal person usually begins to contract after the QRS wave complex arrives. However, the heart of a heart patient may start to contract after a certain time period of the QRS wave complex. For each of the different subjects, the correspondence relationship between the motion state of the subject and the physiological signal of the subject may be determined in process 300, and the physiological signal may be calibrated to determine the motion mode of the target object, thus a time point for triggering the scanning device to scan the subject. At the same time, the position of each scan may be ensured to remain unchanged, avoiding problems such as artifacts in an obtained image by scanning.

In some embodiments, the scanning trigger module 250 may obtaining initial image data of the subject by controlling a scanning device (e.g., the scanning device 160) to scan the subject; and determine the target image data of the subject based on the scan gating information.

The initial image data refers to scanning data used to generate a scanning image.

The determining the target image data of the subject based on the scan gating information may include determining a time period corresponding to the trigger threshold based on the scan gating information; and determine scanning data (i.e., the target image data) in the time period corresponding to the trigger threshold in the initial image data based on the time period corresponding to the trigger threshold.

In some embodiments, a target image of the subject may be generated based on the target image data. The target image refers to an image of the subject generated by the scanning device (e.g., the scanning device 160) based on the target image data.

In some embodiments of the present disclosure, by combining an artificial intelligence (AI) image identification technology with a fast acquisition sequence, a correspondence relationship between a motion mode of the subject and a scan gating waveform of the subject may be found, and an optimal scanning triggering time may be obtained for different person, which may not only be applicable to new types of cardiac scanning triggering, but also to further optimize traditional ECG and finger plethysmography triggering.

It should be noted that the above description of the method 300 for image scanning is merely for illustration, and may not limit the scope of the present disclosure. For those of ordinary skill in the art, various modifications or changes may be made based on the method 300 under the guidance of the present disclosure. However, these modifications and changes are still within the scope of the present disclosure.

Figure 4:
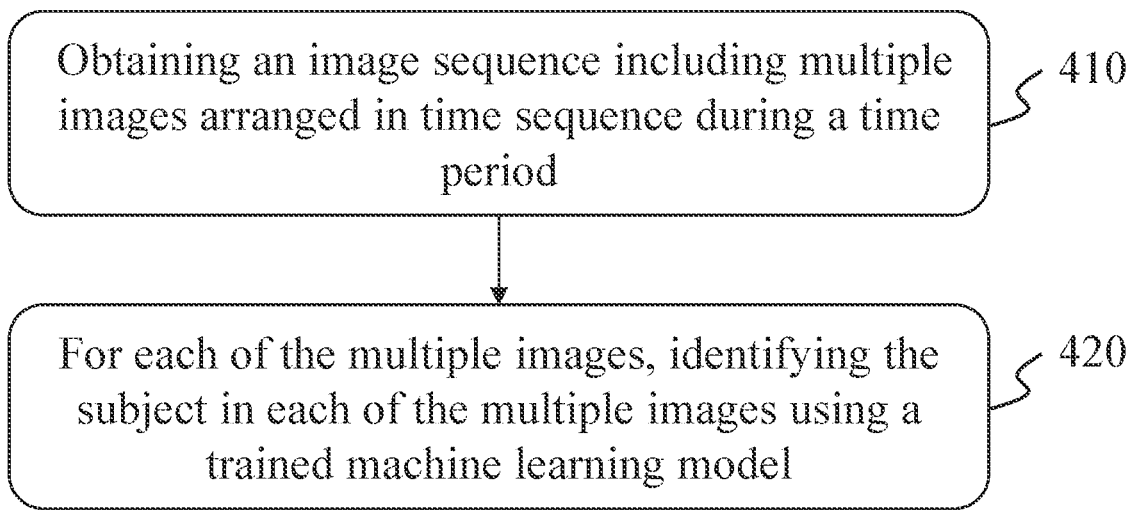
FIG. 4 is a flowchart illustrating an exemplary process for obtaining a target image of a subject based on a trained machine learning model according to some embodiments of the present disclosure.

FIG. 4 is a flowchart illustrating an exemplary process for obtaining a target image of a subject based on a trained machine learning model according to some embodiments of the present disclosure. As shown in FIG. 4, the process for obtaining a target image of a subject based on a trained machine learning model may include following operations.

In 410, an image sequence including multiple images arranged in time sequence during a time period may be obtained. In some embodiments, operation 410 may be performed by the image acquisition module 210.

A duration of the time period may greater than a duration of a motion cycle. In some embodiments, the image acquisition module 210 may acquire the time period from the processing device 110, the user terminal 130, the storage device 140, the image acquisition device 150, the scanning device 160, and/or the physiological signal acquisition device 170. It should be understood that the time period is a time period before triggering the scanning device 160 to scan the subject.

In some embodiments, the image acquisition module 210 may obtain multiple images (also referred to as multiple pre-images) of the subject at multiple time points during the time period acquired by the image acquisition device 150. The image acquisition module 210 may combine a portion of the multiple images of the subject obtained at the multiple time points during a motion cycle in time period in time sequence to obtain image data.

A pre-image refers to an image obtained before triggering the scanning device 160 to scan the subject, which includes the subject. For example, the pre-image may be an image including the subject acquired by the scanning device 160 before triggering the scanning device 160 to scan the subject. As another example, the pre-image may be an image including the subject acquired at a historical time point. Merely by way of example, the pre-image may be an image including the subject acquired by the image acquisition device 150 or the scanning device 160 at a historical time point. As another example, the pre-image may be an image including the subject obtained by the image acquisition device 150 before triggering the scanning device 160 to scan the subject. As another example, before triggering a PET device to scan the heart of a patient, an MRI device may acquire an image including the heart as the pre-image.

More description of the image acquisition module 210 obtaining the multiple images of the subject at the multiple time points during the time period acquired by the image acquisition device 150 may be found elsewhere in the present disclosure, for example, FIG. 1 and the relevant description.

In 420, for each of the multiple images, the subject in each of the multiple images may be identified using a trained machine learning model (also referred to as a first trained machine learning model). In some embodiments, operation 420 may be performed by image acquisition module 210.

The trained machine learning model is a machine learning model used to identify the subject in each of the multiple images. An input of the trained machine learning model may include at least one of the multiple images of the subject, and an output of the trained machine learning model may include images including the identified subject. In some embodiments, the trained machine learning model may include, but may not be limited to, a visual geometry group network (VGG) model, an inception NET model, a full convolutional neural network (FCN) model, a segmentation networks (SegNet) model, a mask region convolutional neural networks (Mask-RCNN) model, or the like.

In some embodiments, a preliminary machine learning model may be trained to obtain the trained machine learning model based on multiple sample images. The multiple sample images with labels may be used as training data to learn parameters of a preliminary machine learning model through a manner (e.g., a gradient descent manner, etc.). A sample image may include a sample pre-image, and a corresponding label may be an image including the identified subject in the sample pre-image.

In some embodiments of the present disclosure, the subject in each of the multiple images may be identified using the trained machine learning model. Thus, interference information (e.g., background images) may be quickly removed from the multiple images of the subject, thus reducing the data processing workload in subsequent processes, making a physiological signal determined based on an image of the subject more accurate.

Figure 6:
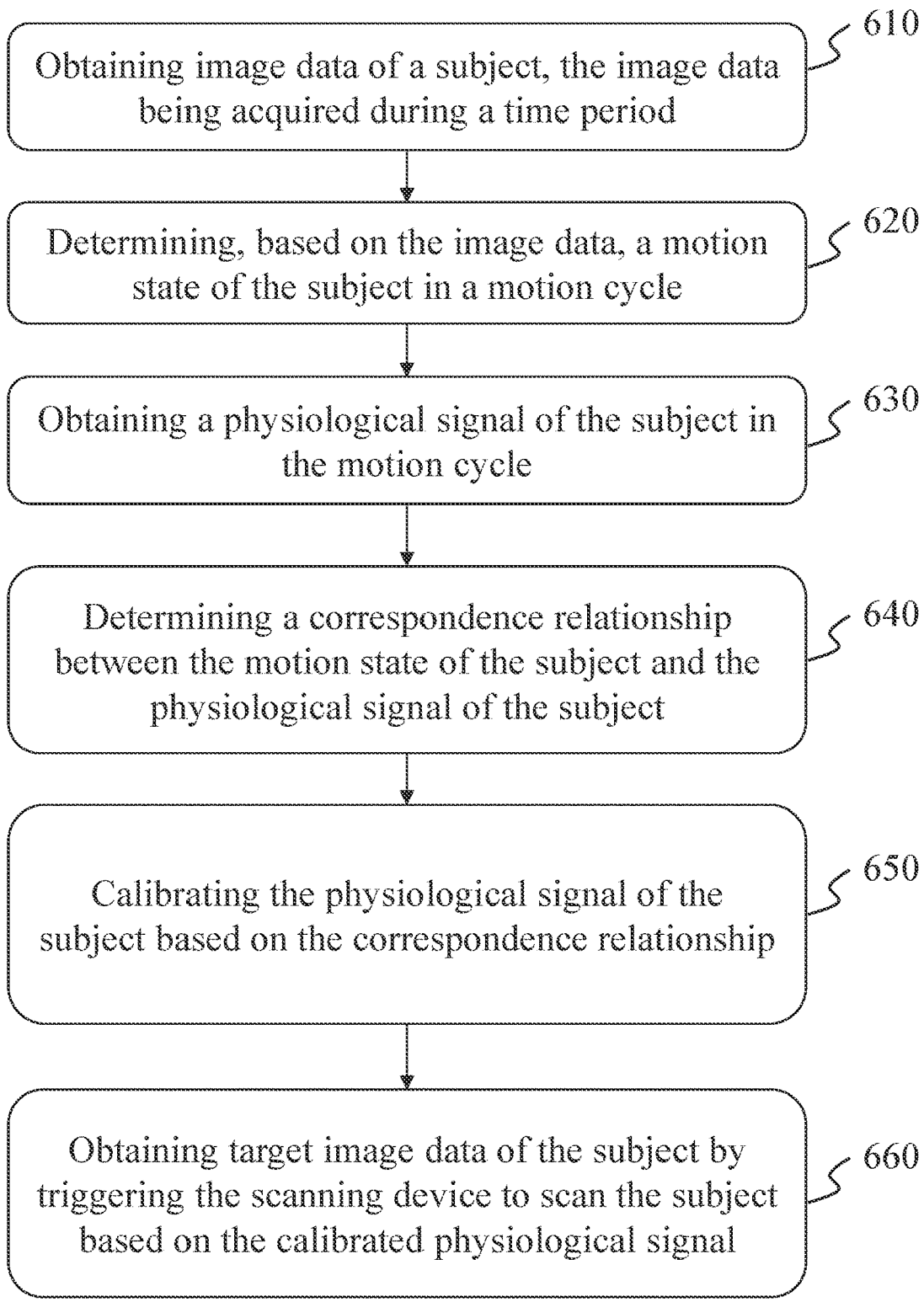
FIG. 6 is a flowchart illustrating another exemplary process for image scanning according to some embodiments of the present disclosure.

FIG. 6 is a flowchart illustrating an exemplary process for image scanning according to some embodiments of the present disclosure. As shown in FIG. 6, process 600 for image scanning may include following operations. In some embodiments, process 600 may be performed by the processing device 110 or the system 200.

In 610, image data of a subject may be obtained. The image data may be acquired during a time period. More description of operation 610 may be found elsewhere in the present disclosure, for example, operation 310 and the relevant description. In some embodiments, operation 610 may be performed by image acquisition module 210.

In 620, a motion state of the subject in a motion cycle may be determined based on the image data. More description of operation 620 may be found elsewhere in the present disclosure, for example, operation 320 and the relevant description. In some embodiments, operation 620 may be performed by the state determination module 220.

In 630, a physiological signal of the subject in the motion cycle may be obtained. More description of operation 630 may be found elsewhere in the present disclosure, for example, operation 330 and the relevant description. In some embodiments, operation 630 may be performed by signal acquisition module 230.

In 640, a correspondence relationship between the motion state of the subject and the physiological signal of the subject may be determined. In some embodiments, operation 640 may be performed by the relationship determination unit of the scan gating information determination module 240.

The motion cycle of the subject may be composed of multiple time points, and there is a correspondence relationship between a physiological signal acquired at each of the multiple time points in the motion cycle and the motion state at the corresponding time point.

Taking FIG. 5 as an example, as shown in FIG. 5, in the motion cycle, a volume of the heart at the time point a is the smallest, therefore time point a is an end stage of cardiac contraction phase. The volume of the heart at the time point b tends to reach a maximum value, therefore time point b is an end stage of a cardiac diastolic phase. Correspondingly, in the electrocardiogram (ECG) of the heart within a motion cycle, a cardiac voltage at the time point a is a cardiac voltage corresponding to the end stage of cardiac contraction phase, and a cardiac voltage at the time point b is a cardiac voltage corresponding to the end stage of the cardiac diastolic phase.

In 650, the physiological signal of the subject may be calibrated based on the correspondence relationship. In some embodiments, a trigger threshold of scan gating information may be determined based on the physiological signal of the subject and the motion state of the subject in the motion cycle. The scan gating information refers to information used to control a scanning device (e.g., the scanning device 160) to scan the subject or used to determine target scanning data from initial scanning data. The trigger threshold of the scan gating information may be calibrated based on the correspondence relationship. In some embodiments, operation 650 may be performed by the signal calibration unit of the scan gating information determination module 240.

In some embodiments, the signal calibration unit may determine a trigger threshold of the scan gating information based on the correspondence relationship between the motion state of the subject and the physiological signal of the subject.

In some embodiments, the signal calibration unit may determine a physiological signal (also referred to as a target physiological signal) corresponding to a slow motion of the subject based on the motion state of the subject in a motion cycle. Based on a time point corresponding to the target physiological signal, a scan gating signal corresponding to the target physiological signal may be determined. The scan gating signal may be designated as the trigger threshold of the scan gating signal. Taking the subject as the heart of a person as an example, the signal calibration unit may determine time points corresponding to the end stage of cardiac contraction phase and the end stage of the cardiac diastolic phase based on the change in volume of the heart in the motion cycle, thereby determining an electric potential corresponding to the end stage of cardiac contraction phase and an electric potential corresponding to the end stage of the cardiac diastolic phase. The signal calibration unit may designate the electric potentials as the trigger threshold.

If the physiological signal of the subject is not calibrated, the trigger threshold may be designated as a default value. For example, a QRS wave complex in the ECG is usually considered as a cardiac contraction phase, and a subsequent 500 ms delay of the QRS wave complex is usually considered as a cardiac diastolic phase with a duration of 0.4 s. A scanning device (e.g., the scanning device 160) may be triggered at a time point (e.g., a time point c shown in FIG. 5) with a subsequent 900 ms delay of the QRS wave complex to obtain an image of the heart. However, due to the variable conditions of patients, motion modes of heart of different patients may also vary, thus the trigger threshold with the default value may not suitable for every patient. For example, the heart of a normal person usually begins to contract after the QRS wave complex arrives. However, the heart of a heart patient may start to contract after a certain time period of the QRS wave complex. For the heart patient, if a scanning operation is directly triggered during the QRS wave complex, an image obtained by the scanning operation may include a lot of artifacts. For example, at the time point c shown in FIG. 5, the heart of the heart patient is still in the cardiac contraction phase, and the image obtained by triggering the scanning device to scan the heart at the time point c may include a lot of artifacts.

In order to achieve a precise scanning trigger for different subject, after calibrating the physiological signal based on the correspondence relationship between the motion state of the subject and the physiological signal of the subject, the signal calibration unit may designate a cardiac voltage corresponding to time point a or a cardiac voltage corresponding to time point b as the trigger threshold. When the cardiac voltage of the subject is the cardiac voltage corresponding to the time point a or the cardiac voltage corresponding to time point b, the scanning device (e.g., the scanning device 160) is triggered to scan the subject, to obtain an image of the subject.

In 660, target image data of the subject may be obtained by triggering a scanning device to scan the subject based on the calibrated physiological signal. In some embodiments, operation 660 may be performed by the scanning trigger module 250. More description of the target image data may be found elsewhere in the present disclosure, for example, FIG. 3 and the relevant description.

In some embodiments, the scanning trigger module 250 may determine the scan gate signal (i.e., a trigger threshold) for triggering the scanning device to scan the subject based on the scan gating information, and obtain a real-time physiological signal of the subject based on the gating signal acquisition device 170. When the real-time physiological signal of the subject may be used for triggering the scanning device to scan the subject, the processing device 110 may determine a real-time scan gating signal for triggering the scanning device to scan the subject based on the trigger threshold, the scanning trigger module 250 may control the scanning device (e.g., the scanning device 160) to scan the subject based on the real-time scan gating signal and obtain the target image data of the subject. For example, when the potential of the heart obtained by an ECG machine is a potential corresponding to the end stage of cardiac contraction phase, the scanning trigger module 250 may control the CT device to scan the heart and generate a CT image of the heart.

In some embodiments, the scanning trigger module 250 may trigger the scanning device to scan the subject through at least one of ECG triggering, finger plethysmography triggering, or a radar triggering based on calibrated physiological signal. For example, when a real-time cardiac voltage is an electric potential corresponding to the end stage of cardiac contraction phase or the end stage of the cardiac diastolic phase, the scanning trigger module 250 may control the scanning device (e.g., the scanning device 160) to scan the subject to obtain the target image data of the subject. When a real-time radar signal is within a radar signal threshold, the scanning trigger module 250 may control the scanning device (e.g., the scanning device 160) to scan the subject to obtain the target image data of the subject. When the real-time finger plethysmography amplitude is within a threshold of finger plethysmography amplitude, the scanning trigger module 250 may control the scanning device (e.g., the scanning device 160) to scan the subject to obtain the target image data of the subject.

In some embodiments, by obtaining image data of the subject acquired during the time period, the motion state of the subject during a motion cycle is determined. The physiological signal of the subject in a motion cycle may be obtained. The correspondence relationship between the motion state of the subject and the physiological signal of the subject is determined, and the scan gating information may be determined based on the correspondence relationship between the motion state of the subject and the physiological signal of the subject. And the target image data of the subject may be obtained by triggering a scanning device to scan the subject based on the scan gating information. It can be understood that different subjects may have different motion modes. For example, a heart of a normal person usually begins to contract after the QRS wave complex arrives. However, a heart of a heart patient may start to contract after a certain time period of the QRS wave complex. For each of the different subjects, the correspondence relationship between the motion state of the subject and the physiological signal of the subject may be determined first in method 600, and the physiological signal may be calibrated to determine the motion mode of the target object, thus a time point for triggering the scanning device to scan the subject. At the same time, the position of each scan may be ensured to remain unchanged, avoiding problems such as artifacts in an obtained image by scanning.

In some embodiments, the scanning trigger module 250 may obtain initial image data of the subject by controlling a scanning device (e.g., the scanning device 160) to scan the subject; and determine the target image data of the subject based on the scan gating information.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of the present disclosure are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
    at least one storage medium including a set of instructions;
    at least one processor in communication with the at least one storage medium, wherein when executing the set of instructions, the at least one processor is directed to cause the system to perform operations including:
        obtaining image data of a subject, the image data being medical image data acquired by a medical scanning device via scanning the subject according to a fast acquisition sequence during a time period;
        determining, based on the image data, a motion state of the subject in a motion cycle;
        obtaining a physiological signal of the subject in the motion cycle;
        determining, based on the motion state of the subject and the physiological signal of the subject, scan gating information of the subject; and
        determining, based on the scan gating information, target image data of the subject, wherein the target image data of the subject is determined by:
            controlling the medical scanning device to scan the subject according to the scan gating information, or
            obtaining initial image data of the subject by controlling the medical scanning device to scan the subject and determining the target image data from the initial image data based on the scan gating information.

2. The system of claim 1, wherein the image data includes an image sequence including multiple images arranged in time sequence, the determining, based on the image data, a motion state of the subject in a motion cycle includes:
    identifying the subject in each of the multiple images using a trained machine learning model; and
    determining the motion state of the subject based on the identified subject.

3. The system of claim 1, wherein the image data includes an image sequence including multiple images arranged in time sequence, the determining, based on the image data, a motion state of the subject in a motion cycle includes:
    determining one or more structure characteristics of the subject in each of the multiple images; and
    determining the motion state of the subject based on the one or more structure characteristics of the subject, wherein the motion state of the subject indicates a change of the one or more structure characteristics in the motion cycle.

4. The system of claim 3, wherein the one or more structure characteristics of the subject include volume of the subject, the determining the motion state of the subject based on the one or more structure characteristics of the subject includes:
    determining the motion state based on a change in the volume of the subject over time.

5. The system of claim 1, wherein the image data includes multiple image sequences acquired in multiple motion cycles, and the determining, based on the image data, a motion state of the subject in a motion cycle includes:
    determining a target image sequence from the multiple image sequences, the target image sequence being an image sequence better representing the motion of the subject than other image sequences in the multiple image sequences; and
    determining, based on the target image sequence, the motion state of the subject in the motion cycle corresponding to the target image sequence.

6. The system of claim 5, wherein the target image sequence is an image sequence obtained when a motion amplitude or a motion intensity in the motion cycle of the subject is within a normal range.

7. The system of claim 5, wherein the target image sequence is an image sequence whose acquisition time is located in a middle position in a time sequence of obtaining the multiple image sequences.

8. The system of claim 1, wherein the motion state of the subject indicates a change of one or more structure characteristics of the subject in the motion cycle, and the determining, based on the motion state of the subject and the physiological signal of the subject, scan gating information of the subject includes:
- obtaining initial scan gating information based on the physiological signal; and
- obtaining the scan gating information of the subject by calibrating the initial scan gating information based on the motion state of the subject.

9. The system of claim 8, wherein the obtaining the scan gating information of the subject by calibrating the initial scan gating information based on the motion state of the subject includes:
- determining a correspondence relationship between the initial scan gating information and the motion state; and
- calibrating the initial scan gating information based on the correspondence relationship between the initial scan gating information and the motion state.

10. The system of claim 9, wherein the calibrating the initial scan gating information based on the correspondence relationship between the initial scan gating information and the motion state includes:
- determining a trigger threshold of the scan gating information based on the correspondence relationship between the initial scan gating information and the motion state; and
- calibrating the initial scan gating information based on the trigger threshold of the scan gating information.

11. The system of claim 1, wherein the determining, based on the motion state of the subject and the physiological signal of the subject, scan gating information of the subject includes:
- obtaining a trained machine learning model; and
- determining, based on the motion state of the subject and the physiological signal of the subject, the scan gating information of the subject using the trained machine learning model.

12. The system of claim 11, wherein the trained machine learning model is obtained via a training process including:
- obtaining a plurality of training samples, each of the training samples including a motion state of a sample object and a physiological signal of the sample object deserved as an input in the training process and reference scan gating information deserved as an output in the training process; and
- training a preliminary machine learning model based on the plurality of training samples.

13. The system of claim 1, wherein the physiological signal of the subject includes an electrocardiogram (ECG), a finger plethysmography, or a motion signal collected by a radar.

14. A system, comprising:
- at least one storage medium including a set of instructions;
- at least one processor in communication with the at least one storage medium, wherein when executing the set of instructions, the at least one processor is directed to cause the system to perform operations including:
  - obtaining image data of a subject, the image data being medical image data acquired by a medical scanning device via scanning the subject according to a fast acquisition sequence during a time period;
  - determining, based on the image data, a motion state of the subject in a motion cycle, wherein the motion state of the subject indicates a change of one or more structure characteristics of the subject in the motion cycle;
  - obtaining a physiological signal of the subject in the motion cycle;
  - determining, based on the motion state of the subject and the physiological signal of the subject, a correspondence relationship between the motion state and the physiological signal;
  - calibrating the physiological signal of the subject based on the correspondence relationship; and
  - obtaining target image data of the subject by triggering the scanning device to scan the subject based on the calibrated physiological signal.

15. The system of claim 14, wherein the calibrating the physiological signal of the subject based on the correspondence relationship includes:
- determining a target physiological signal corresponding to a slow motion of the subject based on the motion state of the subject in the motion cycle and the correspondence relationship; and
- determining the calibrated physiological signal based on the target physiological signal.

16. The system of claim 14, wherein the image data includes multiple image sequences acquired in multiple motion cycles, and the determining, based on the image data, a motion state of the subject in a motion cycle includes:
- determining a target image sequence from the multiple image sequences, the target image sequence being an image sequence better representing the motion of the subject than other image sequences in the multiple image sequences; and
- determining, based on the target image sequence, the motion state of the subject in the motion cycle corresponding to the target image sequence.

17. A method implemented on a computing apparatus, the computing apparatus including at least one processor and at least one storage device, comprising:
- obtaining image data of a subject, the image data being medical image data acquired by a medical scanning device via scanning the subject according to a fast acquisition sequence during a time period;
- determining, based on the image data, a motion state of the subject in a motion cycle;
- obtaining a physiological signal of the subject in the motion cycle;
- determining, based on the motion state of the subject and the physiological signal of the subject, scan gating information of the subject; and
- determining, based on the scan gating information, target image data of the subject, wherein the target image data of the subject is determined by:
  - controlling the medical scanning device to scan the subject according to the scan gating information, or
  - obtaining initial image data of the subject by controlling the medical scanning device to scan the subject and determining the target image data from the initial image data based on the scan gating information.

18. The method of claim 17, wherein the image data includes an image sequence including multiple images arranged in time sequence, the determining, based on the image data, a motion state of the subject in a motion cycle includes:
- identifying the subject in each of the multiple images using a trained machine learning model; and
- determining the motion state of the subject based on the identified subject.

19. The method of claim 17, wherein the image data includes an image sequence including multiple images arranged in time sequence, the determining, based on the image data, a motion state of the subject in a motion cycle includes:

determining one or more structure characteristics of the subject in each of the multiple images; and determining the motion state of the subject based on the one or more structure characteristics of the subject, wherein the motion state of the subject indicates a change of the one or more structure characteristics in the motion cycle.

20. The method of claim 19, wherein the one or more structure characteristics of the subject include volume of the subject, the determining the motion state of the subject based on the one or more structure characteristics of the subject includes:

determining the motion state based on a change in the volume of the subject over time.

\* \* \* \* \*